United States Patent [19]
Elbert et al.

[11] Patent Number: 4,564,631
[45] Date of Patent: Jan. 14, 1986

[54] BAITS FOR COMBATING VERMIN

[75] Inventors: Alfred Elbert, Cologne; Wolfgang Behrenz, Overath; Ingomar Krehan, Cologne, all of Fed. Rep. of Germany

[73] Assignee: Bayer Aktiengesellschaft, Leverkusen, Fed. Rep. of Germany

[21] Appl. No.: 532,237

[22] Filed: Sep. 14, 1983

[30] Foreign Application Priority Data

Sep. 29, 1982 [DE] Fed. Rep. of Germany ....... 3235931

[51] Int. Cl.⁴ ..................... A01N 37/34; A01N 25/00
[52] U.S. Cl. ....................................... 514/521; 424/84
[58] Field of Search ................... 424/304, 84; 514/521

[56] References Cited

U.S. PATENT DOCUMENTS

| 3,026,243 | 3/1962 | Tonelli et al. | 424/211 |
|---|---|---|---|
| 3,272,696 | 9/1966 | O'Connell | 424/84 |
| 3,470,293 | 9/1969 | Geiger | 424/84 |
| 3,591,662 | 6/1971 | Lorenz et al. | 424/210 |
| 4,218,469 | 8/1980 | Fuchs et al. | 424/304 |
| 4,292,325 | 9/1981 | Roman et al. | 424/304 |
| 4,308,262 | 12/1981 | Badmin et al. | 424/304 |

FOREIGN PATENT DOCUMENTS 2382426 9/1978 France .

OTHER PUBLICATIONS

Chem. Abstracts, vol. 94:11649k, (1981).
Chemical Abstracts, vol. 80, No. 5, 2/4/74, p. 110, No. 23525r, Columbus, Ohio, A. P. Gupta et al.: "Effectiveness of Spray–Dust–Bait Combination, Importance of Sanitation in the Control of German Cockroaches in an Inner–City Area".
Chemical Abstracts, vol. 96, No. 3, 18/1/82, p. 110, No. 16035h, Columbus, Ohio, M. G. Ismailov et al.: "Effectiveness of Poisoned Baits".

Primary Examiner—Albert T. Meyers
Assistant Examiner—John M. Kilcoyne
Attorney, Agent, or Firm—Sprung Horn Kramer & Woods

[57] ABSTRACT

An insecticidal bait comprising an insecticidally effective amount of (a) α-cyano-3-phenoxy-4-fluorobenzyl 2,2-dimethyl-3-(β,β-dichlorovinyl)-cyclopropanecarboxylate of the formula

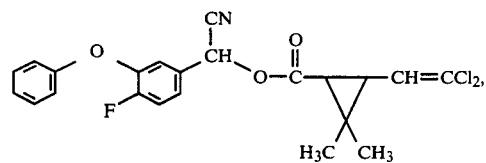

and (b) an insect attracting amount of at least one ingestion attractant. It may also contain additional insecticides, a grinding auxiliary, carrier, adhesive or swelling agent. Surprisingly the principal active ingredient does not repel insects, as do other pyrethroid-like insecticides in baits.

3 Claims, No Drawings

BAITS FOR COMBATING VERMIN

The present invention relates to new baits containing a pyrethroid, a process for the preparation of these baits, and their use for combating vermin.

The appearance of resistance is presenting more and more difficulties in combating domestic vermin. In particular, combating flies has become a great problem, especially in agriculture with animal husbandry. The use of agents for combating the pests at ever shorter intervals of time and with ever increasing concentrations of active compound will therefore become necessary, but is undesirable for the most diverse reasons.

Resistance in flies is widespread. It extends not only to chlorinated hydrocarbons, phosphoric acid esters and carbamates, but occasionally already exists even against the recently developed pyrethroids.

The most common formulations for combating flies are aerosols and oily spraying agents in the home, and emulsion or suspension products in the stall. Since bait formulations of phosphoric acid esters and carbamates are also known for combating flies, development of pyrethroid baits has also been attempted (compare Danish Pest Infestation Laboratory Annual Report, 1978, J. Keiding, "Paint-on-baits", Laboratory tests). However, the baits in question showed only an inadequate action. They have therefore not been developed further, and have achieved no importance in practice. On the basis of the prior art, this was also not surprising, since pyrethroids are known also to exert a considerable ingestion-repellent action on insects, in addition to an insecticidal action.

It is furthermore known that α-cyano-3-phenoxy-4-fluorobenzyl 2,2-dimethyl-3-(β,β-dichlorovinyl)-cyclopropanecarboxylate has very good insecticidal properties and can be converted into the customary formulations, such as solutions, emulsions or suspensions and the like (compare DE-OS [German Published Specification] No. 2,709,264). However, bait formulations based on this active compound have not yet been disclosed.

New baits consisting of
(a) α-cyano-3-phenoxy-4-fluorobenzyl 2,2-dimethyl-3-(β,β-dichlorovinyl)-cyclopropanecarboxylate of the formula

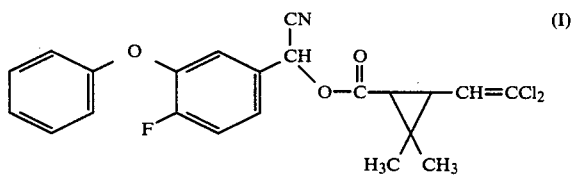

if appropriate as a mixture with one or more active compounds suitable for combating vermin,
(b) at least one ingestion attractant and
(c) if appropriate, formulation auxiliaries, and, if appropriate, other additives, have now been found.

It has furthermore been found that the baits according to the invention are prepared by a process in which α-cyano-3-phenoxy-4-fluorobenzyl 2,2-dimethyl-3-(β,β-dichlorovinyl)-cyclopropanecarboxylate of the formula (I), if appropriate as a mixture with one or more active compounds suitable for combating vermin, is mixed with formulation auxiliaries, if appropriate, and the mixture thereby formed is mixed intensively with at least one ingestion attractant and, if appropriate, with other additives, and if appropriate is then ground.

Finally, it has been found that the baits according to the invention are particularly useful for combating vermin.

It is to be described as extremely surprising that the baits according to the invention which are based on α-cyano-3-phenoxy-4-fluorobenzyl 2,2-dimethyl-3-(β,β-dichlorovinyl)-cyclopropanecarboxylate of the formula (I) are considerably better for combating vermin than the formulations of this active compound which were known hitherto. On the basis of the prior art, it was even to be assumed that the baits according to the invention, like the known bait formulation containing a pyrethroid as the active compound, would exert an ingestion-repellent action on the vermin. Contrary to expectations, however, this is not the case. Rather, a satisfactory degree of action can even be achieved with the aid of the baits according to the invention if far less active compound is applied than in the case of combating vermin with the formulations of the active compound of the formula (I) which were hitherto known. Such a finding could in no way be predicted.

As already mentioned, in addition to the α-cyano-3-phenoxy-4-fluorobenzyl 2,2-dimethyl-3-(β,β-dichlorovinyl)-cyclopropanecarboxylate of the formula (I), the baits according to the invention can also contain one or more other active compounds suitable for combating vermin. Preferred possible active compounds of this type are diethyl-thiono-phosphoryl-α-oximino-phenylacetic acid nitrile and O,O-dimethyl S-(methylaminocarbonylmethyl)-thiolphosphate.

The baits according to the invention furthermore contain at least one ingestion attractant, but can also contain a mixture of different ingestion attractants. Possible ingestion attractants are all the substances usually employed for such a purpose. Preferred substances are protein-containing or carbohydrate-containing substances or their components, such as, for example, milk powder, egg powder, meat extract, alubmins, globulins, aminoacids, malt extracts, flour products and monosaccharides and disaccharides, such as glucose, sucrose and maltose.

Possible formulating auxiliaries in the present case are, in particular, grinding auxiliaries and carriers, and adhesives and swelling agents. An example which may be mentioned of a substance used as a grinding auxiliary or carrier is highly disperse silicic acid. Methylcellulose (=tylose) may be mentioned specifically as an adhesive or swelling agent.

Preferred additives which the baits according to the invention can contain are colorants, preservatives and pheromones which act as insect attractants. Examples of preservatives are 2-hydroxybiphenyl and sorbic acid. Examples of dyestuffs which may be mentioned are azo dyestuffs and phthalocyanine dyestuffs.

The percentage proportions of the components contained in the baits according to the invention can vary within certain ranges. The amount of active compound of the formula (I) is in general between 0.01 and 2.0% by weight, preferably between 0.1 and 1.0% by weight. The baits can contain additional active compounds which are suitable for combating vermin in amounts of 0.1 to 2.0% by weight, preferably 0.25 to 1.5% by weight. Formulation auxiliaries are in general present in amounts of 0.002 to 10.0% by weight, preferably 0.02 to 5.0% by weight. The amounts of grinding auxiliaries or carriers, such as, for example, highly disperse silicic acid, are in general between 0.001 and 4.0% by weight, preferably between 0.02 and 2.0% by weight; the amounts of adhesives or swelling agents, such as, for example, methylcellulose (=tylose) are in general between 0 and 2.0% by weight, preferably between 0 and 1.5% by weight. The percentage proportion of ingestion attractant(s) in the baits according to the invention is in each case calculated as the difference between 100% by weight and the sum of the percentage contents of the remaining components.

All those components which have already been mentioned as preferred in connection with the description of the baits according to the invention can preferably be used in the preparation of the baits according to the invention.

The temperatures in the process according to the invention for the preparation of the new baits can be varied within a certain range. In general, the process can be carried out at temperatures between 10° C. and 30° C., preferably at room temperature.

The process according to the invention is in general carried out by a procedure in which the active compound of the formula (I) and, if appropriate, one or more active compounds suitable for combating vermin, in the particular proportions desired, are mixed, if appropriate, with a formulation auxiliary and the mixture thereby formed is mixed with at least one ingestion attractant, and, if appropriate, further additives, while stirring intensively, and, if appropriate, the mixture is then ground. In principle, however, the components can also be brought together in any other desired sequence. If the bait to be prepared also contains one or more other active compounds suitable for combating vermin, in addition to the active compound of the formula (I), it is advisable to mix each of the active compounds separately with, in each case, at least one formulation auxiliary, to mix the premixes obtained with the remaining components and, if appropriate, to grind the product thereby formed. The components can be mixed using all the mixers usually employed for such purposes. Likewise, the grinding which may be carried out can be effected in all the apparatuses currently used for such purposes.

The baits according to the invention are obtained as powders during their preparation, and can either be applied in this form as scattered baits or converted, after prior mixing with water, into formulations which can be brushed on. If use as scattered baits is intended, it is unnecessary to add adhesives or swelling agents in the preparation. Furthermore, it is not necessary to grind the active compound premixes.

In contrast, if the baits are to be dissolved or dispersed in water before being used, it is useful for adhesives or swelling agents to be present, and grinding of the active compound premixes is also recommended.

The baits according to the invention are outstandingly suitable for combating vermin, and in particular for destroying animal pests in buildings, such as stables, storage rooms, silos and residential buildings. Animal pests, in the present case, is understood as meaning, in particular, insects, such as, for example, flies.

The baits according to the invention are applied either by scattering or by brushing on. If vermin are combated with the aid of scattered baits, the pulverulent material is applied in either the dry or the moist state. It is sufficient to treat one or a few places with a relatively low area. If it is intended to brush on the bait composition, the bait is first mixed with water and the resulting mixture is brushed onto objects in the environment of the vermin to be combated.

The preparation and use of the baits according to the invention can be seen from the following examples.

Preparation examples

EXAMPLE 1

600 g of $\alpha$-cyano-3-phenoxy-4-fluorobenzyl 2,2-dimethyl-3-($\beta,\beta$-dichlorovinyl)-cyclopropanecarboxylate and 400 g of highly disperse silicic acid are mixed intimately in a stirred apparatus. 8.4 g of this premix are mixed intimately with 7.5 g of methylcellulose (=tylose) and 984.1 g of sugar at room temperature and the mixture is then ground. A water-dispersible bait containing 0.5% by weight of $\alpha$-cyano-3-phenoxy-4-fluorobenzyl 2,2-dimethyl-3-($\beta,\beta$-dichlorovinyl)-cyclopropanecarboxylate is obtained in this manner.

EXAMPLE 2

0.133 kg of a premix which consists of 60% by weight of $\alpha$-cyano-3-phenoxy-4-fluorobenzyl 2,2-dimethyl-3-($\beta,\beta$-dichlorovinyl)-cyclopropanecarboxylate and 40% by weight of highly disperse silicic acid, and 0.8 kg of a second premix which consists of 40% by weight of diethylthionophosphoryl-$\alpha$-oximino-phenylacetic acid nitrile and 60% by weight of highly disperse silicic acid are intimately mixed with 0.24 kg of methylcellulose (=tylose) and 30.827 kg of sugar in a Lodige mixer at room temperature and the mixture is then ground. A water-dispersible bait containing 0.25% by weight of $\alpha$-cyano-3-phenoxy-4-fluorobenzyl 2,2-dimethyl-3-($\beta,\beta$-dichlorovinyl)-cyclopropanecarboxylate and 1% by weight of diethyl-thiono-phosphoryl-$\alpha$-oximino-phenylacetic acid nitrile is obtained in this manner.

EXAMPLE 3

A water-dispersible bait containing 0.5% by weight of $\alpha$-cyano-3-phenoxy-4-fluorobenzyl 2,2-dimethyl-3-($\beta,\beta$-dichlorovinyl)-cyclopropanecarboxylate and 1.0% by weight of diethyl-thionophosphoryl-$\alpha$-oximinophenylacetic acid nitrile is prepared by the method described in Example 2.

EXAMPLE 4

A water-dispersible bait containing 0.25% by weight of $\alpha$-cyano-3-phenoxy-4-fluorobenzyl 2,2-dimethyl-3-($\beta,\beta$-dichlorovinyl)-cyclopropanecarboxylate and 1.0% by weight of 0,0-dimethyl S-(methylaminocarbonylmethyl)-thiolphosphate is prepared by the method described in Example 2.

EXAMPLE 5

A water-dispersible bait containing 0.5% in weight of $\alpha$-cyano-3-phenoxy-4-fluorobenzyl 2,2-dimethyl-3-($\beta,\beta$-dichlorovinyl)-cyclopropanecarboxylate and 1.0% by weight of 0,0-dimethyl S-(methylaminocarbonylmethyl)-thiolphosphate is prepared by the method described in Example 2.

Comparative example I

A suspension concentrate consisting of 10% by weight of $\alpha$-cyano-3-phenoxy-4-fluorobenzyl 2,2-dimethyl-3-($\beta,\beta$-dichlorovinyl)-cyclopropanecarboxylate is prepared by mixing $\alpha$-cyano-3-phenoxy-4-fluorobenzyl 2,2-dimethyl-3-($\beta,\beta$-dichlorovinyl)-cyclopropanecarboxylate, highly disperse silicic acid and surface-active substances.

USE EXAMPLES

Example A

Combating flies (Musca spp.) in stables

Bait formulations according to the invention were applied in each case in 20 stables on agricultural farms by converting the particular bait, after prior mixing with water in a ratio of 1:1, into a brushable formulation and applying the formulation, in each case in the desired amounts, to various objects in the stables by means of brushes.

The known suspension concentrate used for comparison was sprayed, in each case in the desired amount, after prior dilution with water.

Stables of comparable size, animal population (cattle and pigs) and severity of infestation by flies were chosen for the experiments.

At certain intervals of time after the treatment, the infestation by flies was determined in all the stables and the action of the product was rated in %. 100% means that a satisfactory degree of action was achieved in all cases, and 0% means that a satisfactory degree of action was achieved in none of the cases.

The products, amounts of active compound and experimental results can be seen from the table which follows.

TABLE A

| | Combating flies (Musca spp.) in stables | | | |
|---|---|---|---|---|
| Product according to example | Amount of active compound in g/100 m² | Degree of action in % after | | |
| | | 4 weeks | 6 weeks | 10 weeks |
| (1) | 1.25* | 94 | 94 | 89 |
| (2) | 0.625* 2.5** | 100 | 100 | 100 |
| (3) | 1.25* 2.5** | 100 | 95 | 100 |
| (4) | 0.625* 2.5*** | 100 | 100 | 100 |
| (5) | 1.25* 2.5*** | 100 | 94 | 94 |
| (I) (known) | 9.0* | 74 | 68 | 58 |

*α-Cyano-3-phenoxy-4-fluorobenzyl 2,2-dimethyl-3-(β,β-dichlorovinyl)cyclopropanecarboxylate
**Diethyl-thionophosphoryl-α-oximino-phenylacetic acid nitrile
***O,O—Dimethyl S—(methylaminocarbonylmethyl)-thiolphosphate

Example B

Combating flies (Musca spp.) in stables

Weight formulations according to the invention were applied in each case in 10 stables in which, a few days to at most 2 weeks before, various pyrethroids had been applied in the form of spraying agents and had not had a satisfactory action, so that resistance to pyrethroids had to be assumed, the bait formulations being applied by converting the particular bait, after prior mixing with water in a ratio of 1:1, into a brushable formulation and applying the formulation, in each case in the desired amounts, to various objects in the stables with brushes.

The known suspension concentrate used for comparison was sprayed, in each case in the desired amount, after prior dilution with water.

Stables of comparable size, animal population (cattle and pigs) and severity of infestation by flies were chosen for the experiments.

At certain intervals of time after the treatment, the infestation by flies was determined in all the stables and the action of the product was rated in %. 100% means that a satisfactory degree of action was achieved in all cases, and 0% means that a satisfactory degree of action was achieved in none of the cases.

The products, amounts of active compound and experimental results can be seen from the table which follows.

TABLE B

| | Combating flies (Musca spp.) in stables | | |
|---|---|---|---|
| Product according to example | Amount of active compound in g/100 m² | Degree of action in % after | |
| | | 4 weeks | 6 weeks |
| (1) | 1.25* | 70 | 70 |
| (3) | 1.25* 2.5** | 100 | 100 |

*α-Cyano-3-phenoxy-4-fluorobenzyl 2,2-dimethyl-3-(β,β-dichlorovinyl)-cyclopropanecarboxylate
**Diethyl-thionophosphoryl- α-oximino-phenylacetic acid nitrile It is understood that the specification and examples are illustrative but not limitative of the present invention and that other embodiments within the spirit and scope of the invention will suggest themselves to those skilled in the art.

We claim:

1. An insecticidal bait comprising an insecticidally effective amount of
   (a) α-cyano-3-phenoxy-4-fluorobenzyl 2,2-dimethyl-3-(β,β-dichlorovinyl)-cyclopropanecarboxylate of the formula

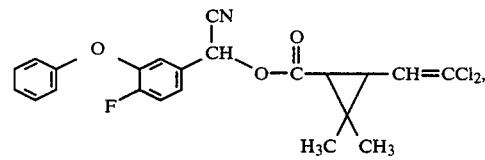

and
   (b) an insect attracting amount of sugar.
2. A bait according to claim 1, wherein (a) is present in about 0.01 to 2% by weight.
3. A bait according to claim 1, further including silicic acid and methyl cellulose.

* * * * *